(12) United States Patent
Belfield et al.

(10) Patent No.: US 8,759,381 B1
(45) Date of Patent: Jun. 24, 2014

(54) TWO-PHOTON ABSORBING WATER SOLUBLE FLUORESCENT PROBE AS A NEAR-NEUTRAL PH INDICATOR

(75) Inventors: Kevin Belfield, Orlando, FL (US); Sheng Yao, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/546,248

(22) Filed: Jul. 11, 2012

Related U.S. Application Data

(62) Division of application No. 12/168,326, filed on Jul. 7, 2008, now Pat. No. 8,232,303.

(60) Provisional application No. 60/948,287, filed on Jul. 6, 2007.

(51) Int. Cl.
*A01N 43/78* (2006.01)
*A61K 31/425* (2006.01)

(52) U.S. Cl.
USPC .......................................................... 514/367

(58) Field of Classification Search
None
See application file for complete search history.

(56) References Cited

U.S. PATENT DOCUMENTS 8,232,303 B1  7/2012  Belfield et al. ................ 514/367

OTHER PUBLICATIONS

Belfield et al. "Fluorene-Based Fluorescent Probes for Two-Photon Imaging Applications". Polymer Preprints (American Chemical Society, Division of Polymer Chemistry), 2006; 47(2):1006-1007.*
Schafer KJ. "Synthesis, Characterization, and Evaluation of New Reactive Two-Photon Absorbing Dyes for Two-Photon Excited Fluorescence Imaging Applications". UCF College of Biomedical Sciences Dissertation, 2005.*
Baruah M, et al. (2005) a highly potassium-selective ratiometric fluorescent indicator based on BODIPY azacrown ether excitable with visible light. Org. Lett. 7(20):4377-4380.
Belfield KD, et al. (2000) Synthesis of New Two-Photon Absorbing Fluorene derivatives via Cu-Mediated Ullmann Condensations. J. Org. Chem. 65(15):4475-4481.
Belfield KD, et al. (2002) a new photosensitive polymeric material for WORM optical data storage using multichannel two-photon fluorescence readout. Chem.materials. 14(9):3656-3662.
Belfield KD, et al. (2004) Photochemical properties of (7-benzothiazol-2-yl-9, 9didecylfluoren-2-yl) diphenylamine under one-and two-photon excitation. J. Photochem.Photobiol. A: Chemistry. 162(2): 569-574.
Belfield KD, et al. (2004) Photostability of a series of two-photon absorbing fluorene derivatives. J. Photochem. Photobiol. A: Chemistry. 162(2):489-496.
Belt JA, et al. (1979) Inhibition of lactate transport and glycolysis in Ehrlich ascites tumor cells by bioflavonoids. Biochemistry. 18(16):3506-3511.

Bizzarri R, et al. (2006) Development of a Novel GFP-based Ratiometric Excitation and Emission pH Indicator for Intracellular Studies. Biophys. J. 90(9):3300-3314.
Charier S, et al. (2004) An efficient fluorescent probe for ratiometric pH measurements in aqueous solutions. Angewandte Chemie. 43(36):4785-4788.
Charier S, et al., (2005) Reactant Concentrations from Fluorescence Correlation Spectroscopy with Tailored Fluorescent Probes. An Example of Local Calibration-Free pH Measurement. J. Am. Chem. Soc. 127(44):15491-15505.
Dey JK, et al. (1991) Solvatochromism and prototropism in 2-(aminophenyl) benzothiazoles. Bull. Chem. Soc. Jpn. 64(10):3142-3152.
Diwu Z, et al. (1999) A novel acidotropic pH indicator and its potential application in labeling acidic organelles of live cells. Chem. Biol. 6(7):411-418.
Dong S, et al. (2004) Synthesis of a New Water-Soluble Polymeric Probe and its Fluorescent Properties for Ratiometric Measurement of Near-Neutral pH. Anal. Letts. 37(14):2937-2948.
EI-Shishtawy RM, et al. (2006) A new Vilsmeier-type reaction for one-pot synthesis of pH sensitive fluorescent cyanine dyes. Tetrahedron. 62(33):7793-7798.
Ertekin K, et al. (2005). Glucose sensing employing fluorescent pH indicator: 4- [(p-N,N-dimethylamino) b enzylidene] -2-phenyloxazole-5 -one. Dyes and pigments. 67(2):133-138.
Hales JM, et al. Nonlinear optical spectroscopic characterization of a series of fluorene derivatives. Proc. SPIE 5211, Nonlinear Optical Transmission and Multiphoton Processes in Organics, 21 (Nov. 4, 2003).
Heikal AA, et al. (2001) Multiphoton molecular spectroscopy and excited-state dynamics of enhanced green fluorescent protein (EGFP): acid-base specificity. Chem. Physics. 274(1):37-55.
Jöbsis PD, et al. (2005) Two-photon excitation fluorescence pH detection using 2, 3-dicyanohydroquinone: a spectral ratiometric approach. J. Microscopy. 217(3):260-264.
O'Brien J, et al. (2000). Investigation of the Alamar Blue (resazurin) fluorescent dye for the assessment of mammalian cell cytotoxicity. Eur. J. Biochem. 267(17):5421-5426.
Thomas JA, et al. (1979) Intracellular pH measurements in Ehrlich ascites tumor cells utilizing spectroscopic probes generated in situ. Biochemistry. 18(11):2210-2218.
Valuk VF, et al. (2005) A wide-range fluorescent pH-indicator based on 3-hydroxyflavone structure. J. Photochem. Photobiol. A: Chemistry. 175(2-3):226-231.
Wiczling P, et al., (2004). Determination of pKa by pH Gradient Reversed-Phase HPLC. Anal. Chem. 76(11):3069-3077.
Zhang Z, et al. (2005) Design, synthesis and evaluation of near-infrared fluorescent pH indicators in a physiologically relevant range. Chem. Commun. 47:5887-5889.
Issue Notification mailed Jul. 11, 2012 for U.S. Appl. No. 12/168,326, filed Jul. 7, 2008 (1 page).

(Continued)

*Primary Examiner* — Leslie A. Royds Draper
(74) *Attorney, Agent, or Firm* — Ballard Spahr LLP

(57) ABSTRACT

Disclosed are fluorescent compounds useful as intracellular pH probes. In particular, the invention teaches a two-photon absorbing, water soluble, fluorescent compound, a fluorene derivative, which is effective as a near-neutral pH indicator and particularly as an intracellular probe. A method for chemical synthesis of the claimed compounds is provided.

6 Claims, 6 Drawing Sheets

(56) References Cited

OTHER PUBLICATIONS

Response to Rule 312 Amendment mailed Apr. 27, 2012 for U.S. Appl. No. 12/168,326, filed Jul. 7, 2008 (3 pages).
Rule 312 Amendment filed Apr. 17, 2012 for U.S. Appl. No. 12/168,326, filed Jul. 7, 2008 (4 pages).
Notice of Allowance and Fees Due mailed Mar. 22, 2012 for U.S. Appl. No. 12/168,326, filed Jul. 7, 2008 (7 pages).
Final Office Action mailed Feb. 29, 2012 for U.S. Appl. No. 12/168,326, filed Jul. 7, 2008 (7 pages).
Response to Non-Final Office Action filed Feb. 13, 2012 for U.S. Appl. No. 12/168,326, filed Jul. 7, 2008 (10 pages).
Non-Final Office Action mailed Nov. 21, 2011 for U.S. Appl. No. 12/168,326, filed Jul. 7, 2008 (6 pages).
Response to Restriction Requirement filed Nov. 7, 2011 for U.S. Appl. No. 12/168,326, filed Jul. 7, 2008 (6 pages).
Restriction Requirement mailed Oct. 6, 2011 for U.S. Appl. No. 12/168,326, filed Jul. 7, 2008 (9 pages).

* cited by examiner

R$^1$, R$^2$, R$^3$, R$^4$=(CH$_2$)$_m$R$^5$, CH$_2$CH$_2$(OCH$_2$CH$_2$)$_m$R$^5$
R$^5$= CH$_3$, COOH, OH, antibodies/antigens, oligopeptides, DNA/RNA fragments, polyamino groups, amine-reactive groups, thio-reactive groups, etc.
m=0-20, n=0-2.
R$^1$, R$^2$, R$^3$, R$^4$ may or may not be the same.

1a R$^1$=phenyl, R$^2$=C$_{10}$H$_{21}$
1b R$^1$=phenyl, R$^2$=C$_2$H$_4$OC$_2$H$_4$OCH$_3$
1c R$^1$=ethyl, R$^2$=C$_2$H$_4$COOH

US 8,759,381 B1

TWO-PHOTON ABSORBING WATER SOLUBLE FLUORESCENT PROBE AS A NEAR-NEUTRAL PH INDICATOR

RELATED APPLICATION

This application claims priority to and is a division of U.S. patent application Ser. No. 12/168,326 filed on Jul. 7, 2008, which claims priority to U.S. Provisional Application Ser. No. 60/948,287 filed on Jul. 6, 2007, the contents of which are incorporated herein by reference in their entirety.

FIELD OF THE INVENTION

The present invention relates to the field of cellular and biological chemistry and, more particularly, to compounds useful as fluorescent pH probes in biological systems.

BACKGROUND OF THE INVENTION

The dynamics of intracellular pH are believed to be crucial for understanding the regulation mechanism of many physiological functions.[1] Of the methods available to determine pH, optical methods have several advantages. These include a rapid response time and a high signal-to-noise ratio. Additionally, they are non-invasive, and they generally have excellent pH sensitivity. Since the first use of a trapped intracellular pH probe, 6-carboxyfluorescein, was described by Thomas et al.[12,31] a large number of intracellular pH indicators has been reported.[1, 4-11] However, these one-photon excited fluorescent pH indicators have serious limitations, e.g. the interference of autofluorescence and scattering from biological fluids and tissue, photodamage of the samples and photobleaching of the indicators, difficulty in analyzing intercellular or intracellular pH differences, and others. Recently, using two-photon fluorescence (2 PF) to measure the pH has gained attention.[12-15] Advantages of using the two-photon approach include less scattering and deeper penetration in biological samples by using NIR excitation light, less photodamage and photobleaching, as well as the unique properties of obtaining 3D resolution.

In addition to normal fluorescence methods, a 2 PF indicator has also been employed to detect the pH at molecular level by using fluorescence correlation spectroscopy.[14] In order to quantitatively measure pH, the pK, of the indicator needs to match with the pH of the experimental system. Since the pH in the cell cytosol is typically between 6.8 and 7.4, there is tremendous interest in the development of an efficient two-photon absorbing (2 PA), near-neutral, fluorescent pH indicator. However, near-neutral 2 PF pH indicators are rare and the 2 PA cross-sections of most commercial pH indicators in the NIR region are low.[12-15] Only recently, one example of a pH indicator designed with emphasis on improving the two-photon absorptivity was reported by Charier et al.[13] A relatively high value of 60 GM (1 GM=$10^{-50}$ cm$^4$ s photon$^{-1}$) was described, but its pKa of 5.7 is too low for near-neutral biological applications.

SUMMARY OF THE INVENTION

With the foregoing in mind, the present invention advantageously provides water-soluble fluorene derivatives with $pK_a$ value near 7.

These compounds were synthesized and their potential as 2 PF pH indicators was evaluated. Their $pK_a$ value makes them ideal for biological and biomedical imaging and diagnostic applications.

The general structure of the fluorophore is shown in FIG. 1. Fluorene derivative 1c has the same D-π-A type backbone 7-(benzo[d]thiazol-2-yl)-N,N-dipheny 9H-fluoren-2-amine other 2 PA chromophores (1a and 1b, FIG. 1) developed in our group, and is used as an example.[16] The compounds 1a and 1b have been demonstrated to possess high 2 PA cross-sections, i.e. ~100 GM, almost unity fluorescent quantum yield and high photostability.[17, 18] However, these two compounds are rather hydrophobic, which limited their applications in aqueous biological environments. Therefore, compound 1c is specifically designed to improve the water-solubility by introduction of the dipropionic carboxylic acid at 9-position of the fluorene ring, and the diphenylamino groups in 1a and 1b were replaced by diethyltheamino group to adjust the $pK_a$ into proper biological pH range.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

FIGS. 1 through 5 illustrate the presently disclosed invention, a two-photon absorbing, water soluble, fluorescent compound which is effective as a near-neutral pH indicator and, particularly, as an intracellular pH probe.

Figure 1:
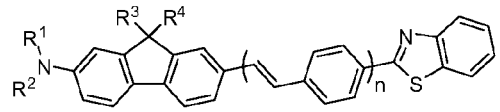
FIG. 1 shows the general structure of fluorene derivatives and a chemical synthesis of fluorescent probe 1 according to an embodiment of the present invention.
Figure 1:
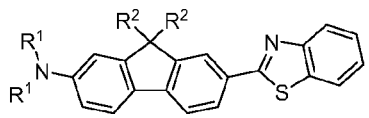
Figure 1:
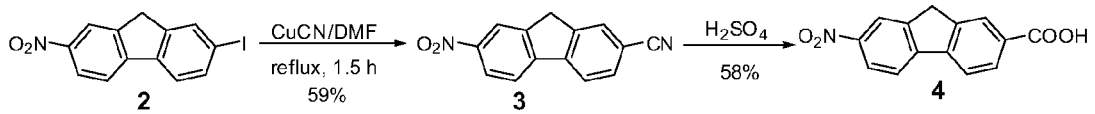
Figure 1:
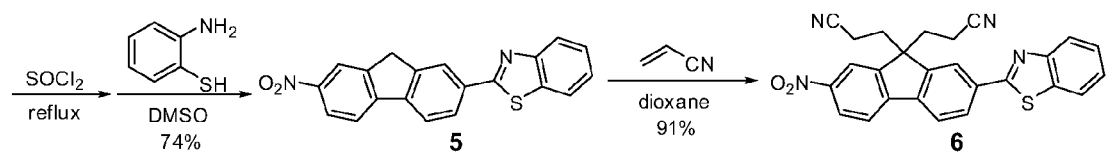
Figure 1:
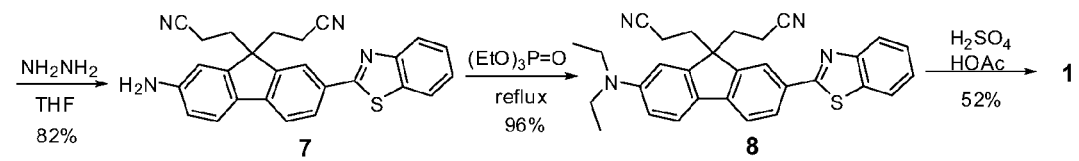

The synthesis of the disclosed compounds is shown in the chemical reactions depicted in FIG. 1. Converting the iodo group in 2 into cyano in 3 gave the precursor that can be easily hydrolyzed to carboxylic acid 4. The carboxylic acid was then transformed to acid chloride in situ and reacted with aminothiophenol in DMSO to form the benzothioazole derivative. Two propionitrile groups were then introduced to 5 by a Michael reaction. Subsequent reduction of the nitro to amino group, diethylation of the amine with triethylphosphate, and hydrolysis of the nitrile groups afforded the final product 1c in good overall yield. All compounds were fully characterized by NMR and elemental analysis (or HRMS in case of compounds with carboxylic acid moieties).

Figure 2:
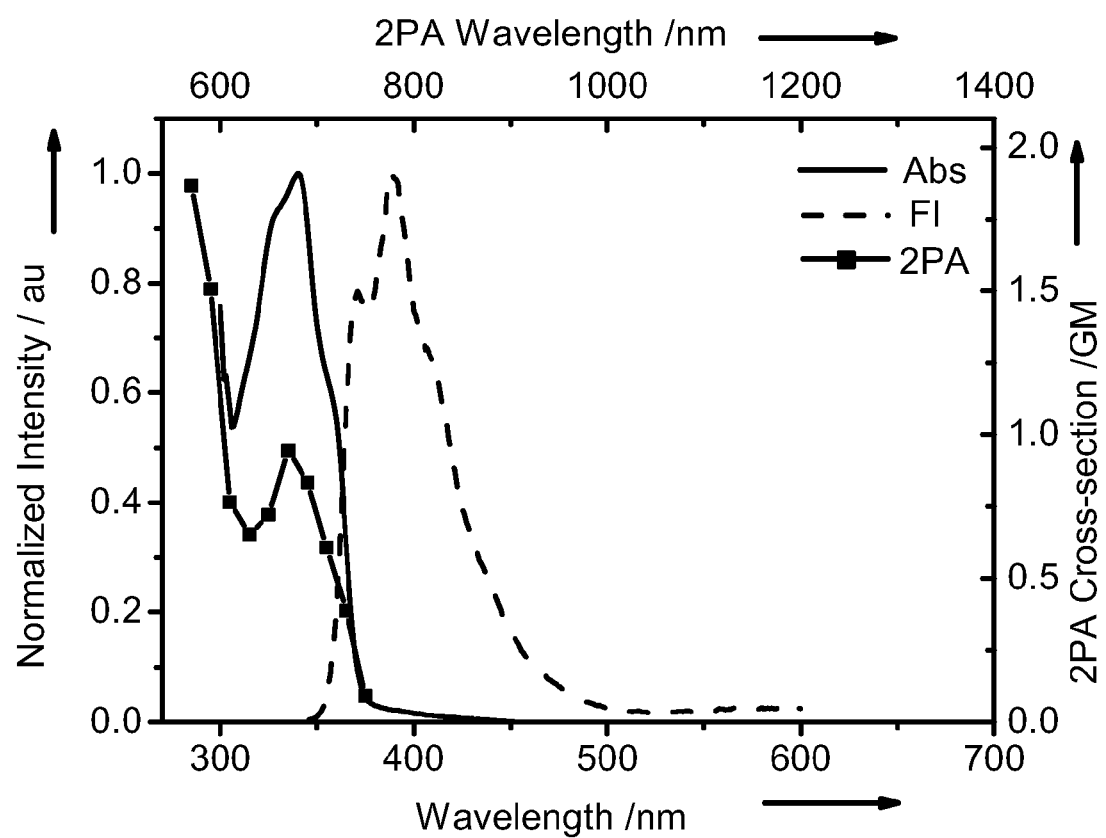
FIG. 2 graphically illustrates the absorption, emission and two-photon excitatin (2 PE) spectra of (A) protonated form 1 cH$^+$ (in pH=4 buffer) and (B) neutral form 1c (in pH=10 buffer)—absorption and fluorescence spectra are normalized.
Figure 2:
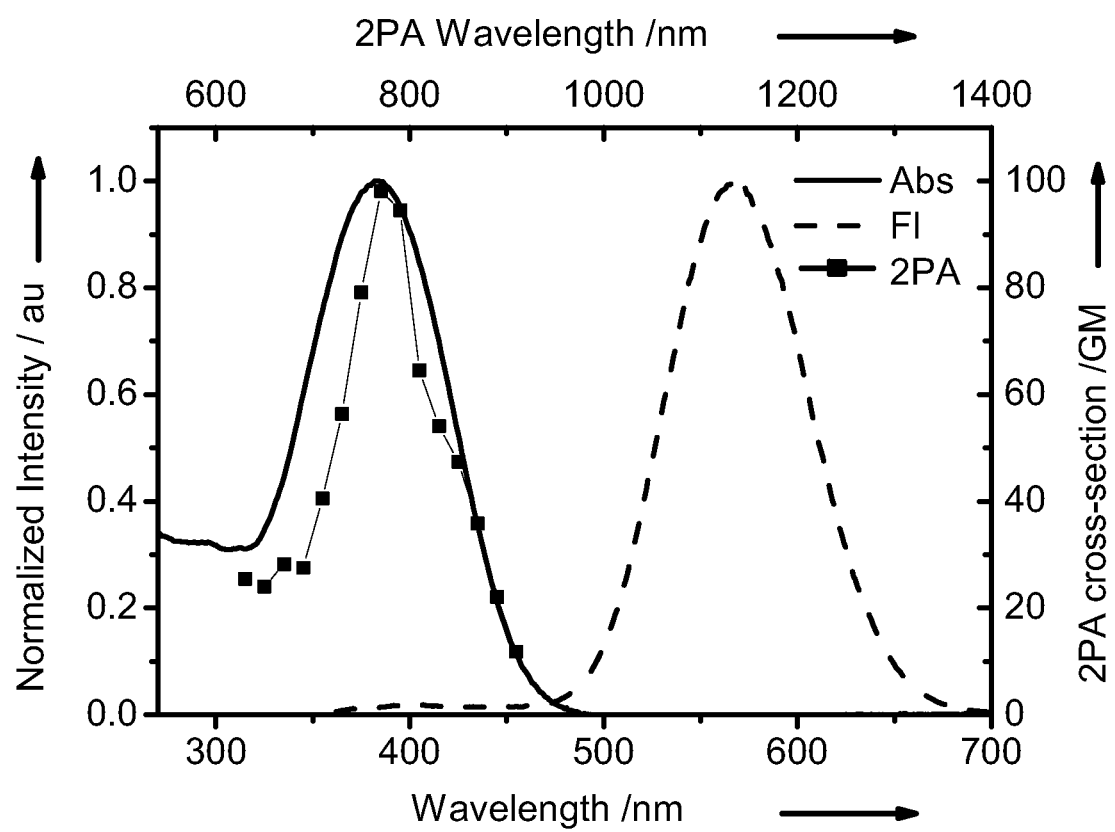
Figure 3:
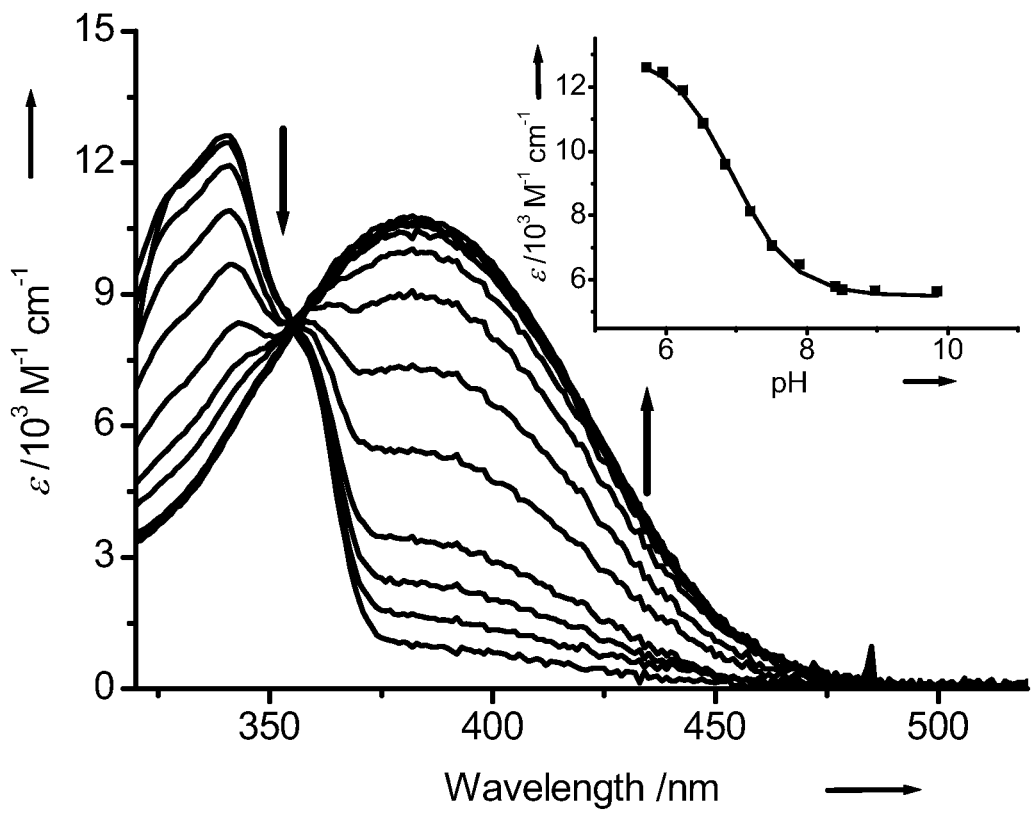
FIG. 3 depicts the pH dependence of the absorption spectra of probe 1c in buffer at 0.01 mM, with arrows indicating the change of the absorption intensities with pH increase—the inset shows the nonlinear fitting of the pH dependence of molar extinction coefficients at 341 nm.

As expected, compound 1c exhibits adequate water solubility, i.e. $>10^{-4}$ M at pH 1-7 and $>10^{-3}$ M at pH 7-12. At pH 4, the absorption and emission maxima of protonated 1c are 341 nm and 391 nm, respectively (FIG. 2, left panel) and a fluorescence quantum yield of 0.21 was recorded. The 2 PA cross-section of the dye is very low in the excitation wavelength range of 570 nm to 750 nm, which may be attributed to very strong electron withdrawing nature of the protonated nitrogen of the diethylamino group (see the $pK_a$ measurement). In this nearly centrosymmetric A-π-A type structure, the absorption wavelength is expected to shift to shorter wavelength and the single photon excitation allowed $S_0$-$S_1$ transition is not allowed by two-photon excitation.[19] In contrast, at pH 10 buffer, where a neutral form of 1c predominates, the absorption maxima is red shifted 41 nm to 382 nm, and fluorescence quantum yield increased to 0.56 (FIG. 2, right panel). In addition. a dramatic increase of 2 PA cross-section to 99 GM at the excitation wavelength of 770 nm occurred. Since the neutral form of dye 1c is a D-π-A type structure, it is well-known that the single-photon excitation of the allowed $S_0$-$S_1$ also occurs via two-photon excitation, which in this case is the absorption band at 382 nm.[19]

Figure 4:
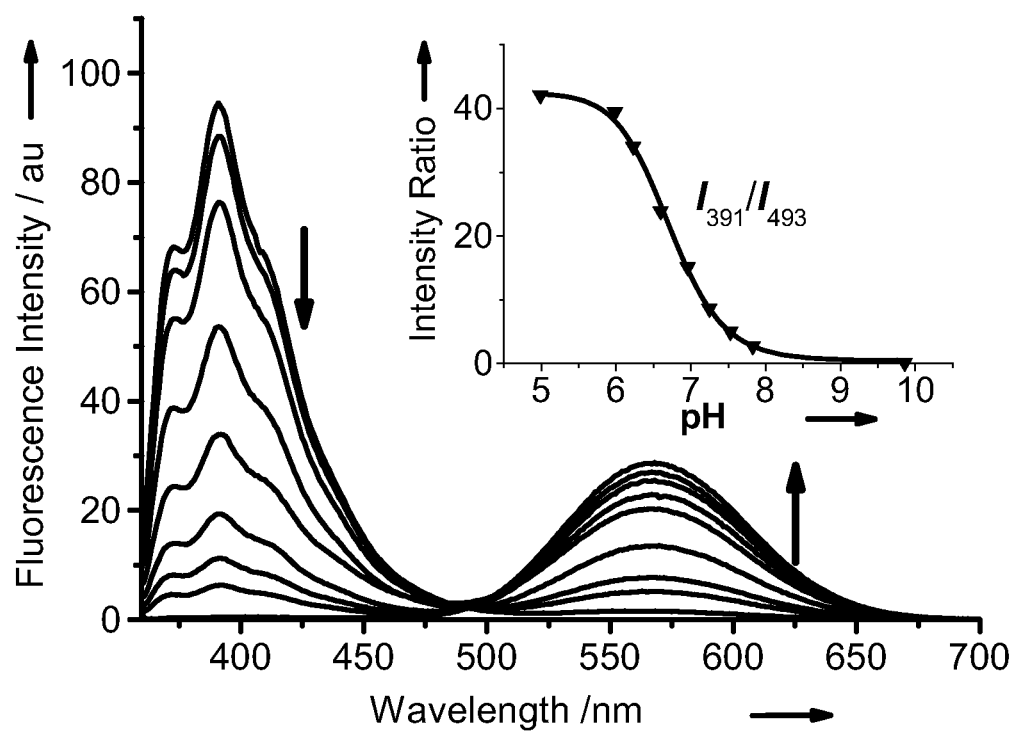
FIG. 4 shows pH-dependence of the fluorescence intensity of 1c in buffer (10-5 M) excited at 355 nm—the inset is the ratiometric calibration curves of $I_{391}II_{493}$ (intensity at 391 nm vs. intensity at isoemissive point 493 nm)

The pH dependence of the absorption spectra when titrated in aqueous buffer is shown in FIG. 4. With the increase of pH, the absorption peak at 341 nm, attributed to the protonated form of 1c, becomes weak and the absorption of the neutral form at 382 nm appears with a well-defined isosbestic point. It is known that the basicity of the nitrogen of diethylaminobenzene[20] is much stronger than the nitrogen in benzothiazole.[21-22] Hence, the structure protonated form of 1c is assigned as protonated at diethylamino site. The inset in FIG. 4 shows the results of the nonlinear regression of the £ at 341 nm according to an existing method[23] which gave a $pK_a$ value of 6.95±0.01. The $pK_a$ value may also be calculated from pH dependence of the integrated fluorescence of 1c excited at 340 nm and 382 nm, taking advantage of well separated fluorescence bands of the two forms. By using similar nonlinear regression, nearly the same $pK_a$ value was obtained (6.96±0.04).

In practical applications, fluorescent indicators with ratiometric properties are highly desirable since the ratio of the fluorescence intensity at peak wavelength vs insensitive isoemissive wavelength is constant, regardless of the change of fluorophore concentration by photobleaching or change of the external environment, such as ion concentration. When 1c was excited at the wavelength of the isosbestic absorption point (355 nm), the fluorescence from both protonated and neutral forms was observed, as shown in FIG. 4. The distinguished isoemission point at 493 nm makes 1c an excellent ratiometric pH indicator. Under two-photon excitation, the fluorescence from the protonated form disappeared due to its low 2 PA cross-section, rendering it unsuitable as a two-photon ratiometric pH indicator. However, the high 2 PA cross-section and high fluorescence quantum yield of the neutral form makes it promising for a number of important applications in fluorescence correlation spectroscopy and intra and extracelluar pH sensing.

Figure 5:
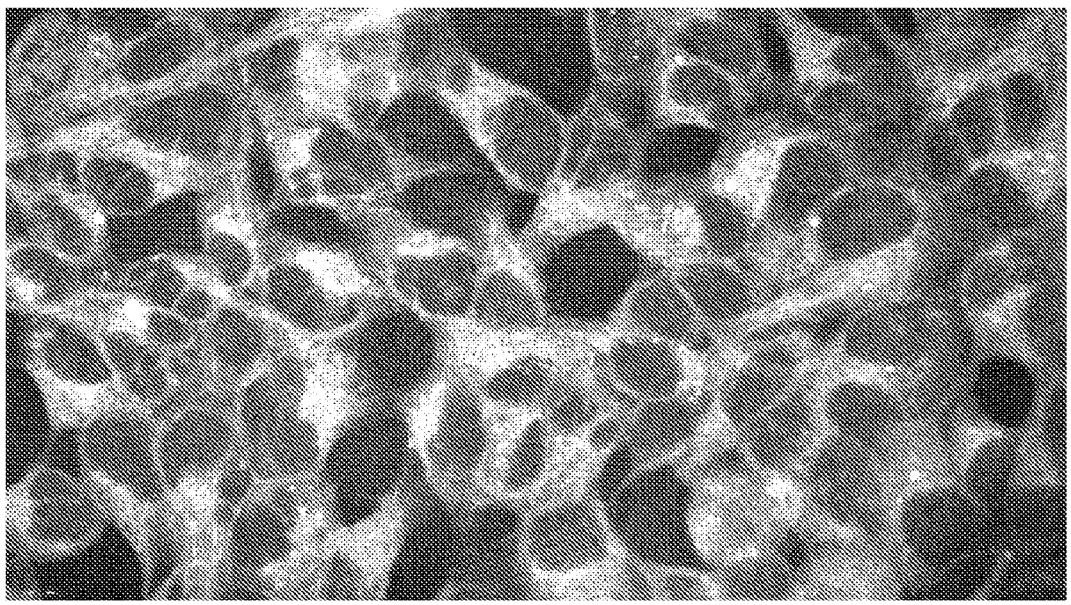
FIG. 5 shows a 2 PF image of NT2 cells incubated with 1c.

For intracellular applications, one major concern for the probes is the cell permeativity of the indicator. Therefore, 1c was incubated with NT2 (NTERA-2 cl.D1 [NT2/D1]) cells. The two-photon fluorescence image of the stained cells is shown in FIG. 5. The dye has good permeativity and disperses in the cytosol well. The cytotoxic effect of 1c on proliferating cells is another parameter of primary interest, particularly for any live-cell fluorescence imaging applications. An Alamar Blue (AB) reduction analysis[24] was used to assess the cytotoxicity of 1c on proliferating NT2 cells. The cells were treated with different concentrations of compound 1c (0.1 μM-100 μM) dissolved in buffer, and were also treated with 10% AB solution. The observed fluorescence intensity of AB reduction by cells treated with various doses of 1c was similar to that observed for cells untreated without any fluorene probe (control) after 48 h, indicating low toxicity of 1c over a relatively wide concentration range.

In summary, fluorene derivatives 1a, 1b and 1c were synthesized and tested. Derivative 1c functions as a near-neutral pH indicator with $pK_a$ of 6.96, confirmed by both absorption and fluorescence methods. The distinct isoemissive point in the fluorescence spectra at different pH levels, good dispersion in the cell cytosol, and low cytotoxicity indicates that 1c satisfies all the criteria for an excellent ratiomeric fluorescent pH indicator. Furthermore, its high 2 PA cross-section also shows it has great potential for 3D pH fluorescence mapping in live and fixed cells, as demonstrated in FIG. 5.

The invention, therefore, includes a fluorescent compound preferably according to formula 1c, as shown below, wherein $R^1$=ethyl and $R^2$=$C_2H_4COOH$.

Compound 1c

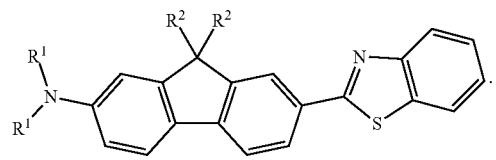

Another compound according to the invention has formula 1a, as shown below, wherein $R^1$=phenyl and $R^2$=$C_{10}H_{21}$.

Compound 1a

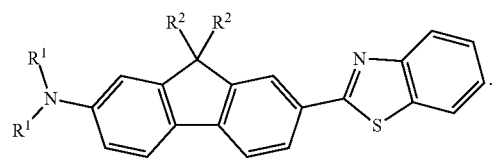

A third compound according to the invention has formula 1b, as shown below, wherein $R^1$=phenyl and $R^2$=$C_2H_4OC_2H_4OCH_3$.

Compound 1b

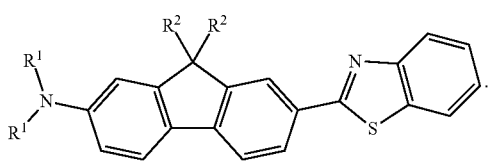

The invention additionally includes a biologically compatible composition containing preferred compound 1c, but the composition may contain compounds 1a, 1b, or combinations of all three compounds. A biologically compatible composition is one which is compatible with the fluorescent compounds herein disclosed, for example, by not quenching the fluorescence, and which can safely be administered to living cells without causing undue toxicity to the cells. An example of such a biologically compatible composition would be a buffering solution.

Another aspect of the invention is a method of sensing pH inside a cell, the method comprising introducing the fluorescent compound into the cell and irradiating the cell with a near-infrared wavelength. More broadly, a method of sensing pH inside a cell may comprise introducing the fluorescent compound into the cell and irradiating the cell with a wavelength effective for exciting the compound to fluoresce approximately at a predetermined pH. On a larger scale, the method of sensing pH may be applied to a biological sample, the method comprising contacting the biological sample with the fluorescent compound and irradiating the biological sample with a near-infrared wavelength. Likewise, in the method comprising contacting the biological sample with the fluorescent compound, irradiating the biological sample may be accomplished with a wavelength effective for exciting the compound to fluoresce approximately at a predetermined pH.

The present invention also includes a method of synthesizing a two-photon absorbing, near-neutral, pH indicator fluorescent when excited by light of a near-infrared wavelength and having a formula selected from compounds 1a, 1b and 1c. The method of synthesis comprises a reaction sequence according to Scheme 1, as set forth in FIG. 1.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES CITED

1. R. P. Itaugland, M T. Z. Spence, I. Johnson, A Basey, in *The Handbook: A Guide to Fluorescent Probes and Labeling Technologies*, 10th Ed: cd Molecular Probes, Invitrogen Detection Technologies Carlsbad, 2005, pp 935 and references therein.
2. J. A. Thomas, R. N. Buchsbaum, A. Zimniak, E Recker, *Thochem*. 1979, 18, 2210.
3. J. A. Belt, J A Thomas, R_N. Buchsbaum, E Recker, *Ellochem*. 1979, 18, 3506.
4. R. M. El-Shishtawy, P. Almeida, *Tetra*. 2006, 62, 7793.
5. R. Bizzarri, C. Arcanpli, D. Arosio, F. Ricci, P. Faraci, F. Cardarelli, F. Beltram, *Biophys. J.* 2006, 90, 3300.
6. Z. Zhang, S. Achilefu, *Chem. Comm.* 2005, 5887.
7. V. F. Valuk, Duportail, V. G. Pivovarenko. J. *Photochem Photobiol. A: Chem*. 2005, 175 226.
8. M. Baruah, W. Qin, N. Basanc, W. M. DeBorggraeve, Boens, *J. Org. Chem.* 2005, 70, 4152.
9. K. Enekin, S. Cinur, T. Aydemir, S. Alp, *Dye Pigment*. 2005, 67, 133.
10. S. Dong, H. Ma, X. Li, M. Sun, X. Duan, *Anal. Lett.* 2004, 37, 2937.
11. Z. Diwu, C. S. Chat, C. Zhang, D. II. Klauben, R. P. Halleffild, *Chem. Biol.* 1999, 6, 411.
12. A. A Heikal S. T. Hess, W. W. Webb, *Chem. Phis.* 2001, 274, 37.
13. S. Charier, O. Ruel, J.-B. Baudin, D. Alcor, J.-F. Allemand, A Meglio, L. Jullien, *Angew. Chem. Intern. Ed* 2004, 43, 4785.
14. S Charier, A. Meglio, D. Alcor, E. Cogne-Laage, J. F. Allemand, I. Jullien, A Lemarchand, *J. Am. Chem. Soc.* 2005, 127, 15491.
15. P. D. Joebsis, C. A. Combs, R. S. Balaban, *J. Microscopy* 2005, 217, 260.
16. K. D. Belfield, K. J. Schafer, W. Mourad, B. A. Reinhardt, *J. Org. Chem.* 2000, 65, 4475.
17. K. O. Belfield, M. V. Bandar, 0. V. Przhoriska, K_J. Schafer, *J. Photochem. Photobiol. A: Chem* 2004, 162, 489.
18. K. D. Belfield, M. V. Bonder, 0. V. Przhonska, K. J. Schafer, *J. Photochem. Photobiol. A: Chem.* 2004, 162, 569.
19. 1. M. Hales, K. J. Schafer, A. M. Morales, K. D. Belfield, D. J. Hagan, F. W. Van Stryland, *Proc. SPIE-Intern. Soc. Opt. Eng.* 2003, 5211, 21.
20. P. Wiczling, M. J. Markuszewski, R. Kaliszan, *Anal. Chem.* 2004, 76, 3069.
21. K. D. Belfield, K. J. Schafer, *Chem. Mater.* 2002, 14, 3656.
22. J. K. Dey, S. K. Oogra, *Bull. Chem. Soc. Japan* 1991, 64, 3142.
23. E. J. Billo, in *Excel for Chemists, A Comprehensive Guide*, Wiley-VCI I: New York, 1997, pp. 303.
24. J. O'Brien, I. Wilson, T. Orton, F. Pognan, Ever. *J. Biochem.* 2000, 267, 5421.

That which is claimed:

1. A method of sensing pH inside a cell, the method comprising introducing a fluorescent compound having the following structure

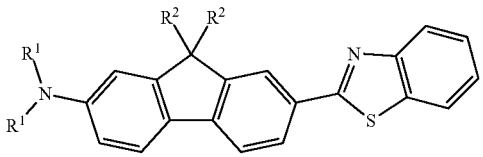

into the cell, irradiating the cell with a near-infrared wavelength, detecting fluorescence from the compound, and associating the fluorescence with a pH, wherein $R^1$=ethyl and $R^2$=$C_2H_4COOH$.

2. The method of claim 1, wherein the near-infrared wavelength is effective for exciting the compound to fluoresce.

3. The method of claim 1, wherein associating the fluorescence with a pH comprises comparing the detected fluorescence with a set of pre-determined pH values corresponding to fluorescence from the compound measured at a plurality of pHs.

4. A method of sensing pH in a biological sample, the method comprising contacting the biological sample with a fluorescent compound having the following structure

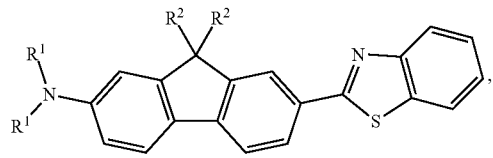

irradiating the biological sample with near-infrared radiation, detecting fluorescence from the compound, and associating the fluorescence with a pH, wherein $R^1$=ethyl and $R^2$=$C_2H_4COOH$.

5. The method of claim 4, wherein the near-infrared radiation is effective for exciting the compound to fluoresce.

6. The method of claim 4, wherein associating the fluorescence with a pH comprises comparing the detected fluorescence with a set of pre-determined pH values corresponding to fluorescence from the compound measured at a plurality of pHs.

* * * * *